United States Patent [19]

Arrowsmith et al.

[11] Patent Number: 4,647,565

[45] Date of Patent: Mar. 3, 1987

[54] 2-(2-QUINAZOLINYLAMINOALKOXYME-THYL)-1,4-DIHYDROPYRIDINE DERIVATIVES AS CARDIOVASCULAR AGENTS

[75] Inventors: John E. Arrowsmith; Simon F. Campbell, both of Deal; Peter E. Cross, Canterbury; Roger P. Dickinson, Dover, all of England

[73] Assignee: Pfizer Inc., New York, N.Y.

[21] Appl. No.: 741,416

[22] Filed: Jun. 5, 1985

[30] Foreign Application Priority Data

Jun. 7, 1984 [GB] United Kingdom ............... 8414518

[51] Int. Cl.$^4$ .................. A61K 31/505; A61K 31/47; C07D 401/12; C07D 401/14
[52] U.S. Cl. .................. 514/260; 514/313; 544/284; 544/293; 546/162; 546/193; 546/284; 546/321; 546/322
[58] Field of Search .................. 544/284; 514/260

[56] References Cited

U.S. PATENT DOCUMENTS 4,341,893 7/1982 Manoury ............... 544/284

Primary Examiner—Glennon H. Hollrah
Assistant Examiner—James H. Turnipseed
Attorney, Agent, or Firm—Charles J. Knuth; Albert E. Frost; James M. McManus

[57] ABSTRACT

Dihydropyridines of the formulae

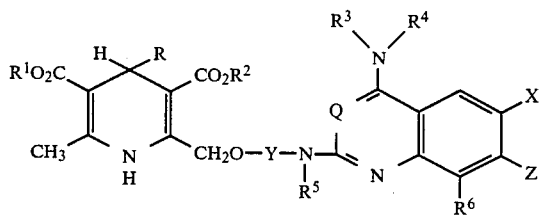

and

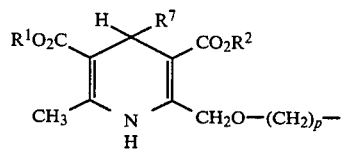

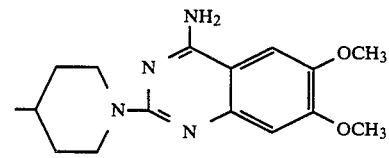

wherein R is chlorothienyl or mono- or disubstituted phenyl where said substituent is fluoro, chloro, bromo or trifluoromethyl; $R^1$ and $R^2$ are each alykl; $R^3$ and $R^4$ when taken separately are each hydrogen or alkyl; $R^3$ and $R^4$ when taken together with the nitrogen to which they are attached are piperidine or pyrrolidine; $R^5$ is alkyl or 2-hydroxyethyl; $R^6$ is hydrogen or methoxy; X and Z are each hydrogen or methoxy; Y is alkylene; $R^7$ is chlorophenyl or trifluoromethyl-chlorophenyl; p is 0 or 1; and Q is CH or N are useful in the treatment of hypertension, heart failure and angina.

16 Claims, No Drawings

2-(2-QUINAZOLINYLAMINOALKOXYMETHYL)-1,4-DIHYDROPYRIDINE DERIVATIVES AS CARDIOVASCULAR AGENTS

BACKGROUND OF THE INVENTION

This invention relates to cardiovascular agents and in particular to certain 1,4-dihydropyridines which combine both calcium antagonist and alpha$_1$-antagonist activity and which are useful for the treatment of hypertension, heart failure and angina.

The dihydropyridine calcium antagonists are well known as a class of therapeutic agents, the most widely used example being the compound nifedipine. Dihydropyridine derivatives substituted at the 2-position by side chains which include varous groups have been described in our published European patent applications nos. 60674 and 100189. Such compounds can reduce the movement of calcium into the cell and they are thus able to delay or prevent the cardiac contracture which is believed to be caused by an accumulation of intracellular calcium under ischaemic conditions. Excessive calcium influx during ischaemia can have a number of additional adverse effects which would further compromise the ischaemic myocardium. These include less efficient use of oxygen for ATP production, activation of mitochondrial fatty acid oxidation and possibly, promotion of cell necrosis. Thus calcium antagonists are useful in the treatment or prevention of a variety of cardiac conditions, such as angina pectoris, cardiac arrythmias, heart attacks and cardiac hypertrophy. Calcium antagonists also have vasodilator activity since they are thus also useful as antihypertensive agents and for the treatment of coronary vasospasm. Howver, with respect to the vasculature, calcium antagonists are primarily arteriolar dilators and the reflex sympathetic activation which occurs with nifedipine-like agents can be detrimental for both hpertensive and anginal patients. Alpha-$_1$-antagonits such as prazosin and doxazosin are also effective antihypertensive drugs but, since these agents act on both venous and arteriolar tone, heart rate changes are minor. In addition, alpha$_1$-antagonists have beneficial effects on high-density/low-density lipoprotein levels.

Combination of calcium- and alpha$_1$-antagonist properties in accordance with the present invention is advantageous since the clinical benefits associated with both pharmacological activities can be provided by a single agent. For example, these compounds possess anti-ischaemic, venodilator and arteriolardilator properties and are effective for the treatment of a wide range of cardiovascular disorders, particularly hypertension, heart failure and angina.

Quinazoline-dihydropyridines are disclosed as useful cardiovascular agents in U.S. application Ser. No. 562,482 filed Dec. 16, 1983 now U.S. Pat. No. 4,572,908.

SUMMARY OF THE INVENTION

Thus, according to the present invention, there are provided 1,4-dihydropyridine derivatives of the formulae:

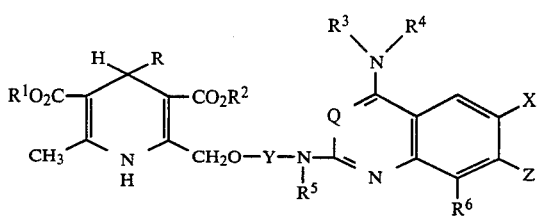

and

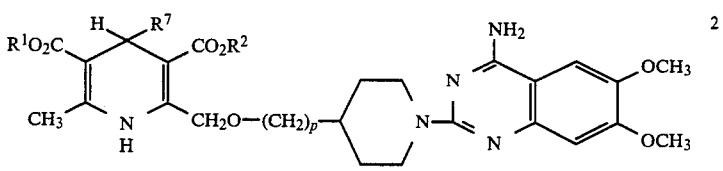

and pharmaceutically acceptable salts thereof where R is chlorothienyl or mono- or disubstituted phenyl where said substituent is fluoro, chloro, bromo or trifluoromethyl; $R^1$ and $R^2$ are each alkyl of one to three carbon atoms; $R^3$ and $R^4$ when taken separately are each hydrogen or alkyl of one to three carbon atoms; $R^3$ and $R^4$ when taken together with the nitrogen to which they are attached are pyrrolidine or piperidine; $R^5$ is alkyl of one to three carbon atoms or 2-hydroxyethyl; $R^6$ is hydrogen or methoxy; X and Z are each hydrogen or methoxy; Y is alkylene of two to three carbon atoms; $R^7$ is chlorophenyl or chloro-trifluoromethylphenyl; p is an integer of 0 or 1; and Q is CH or N.

A preferred group of compounds are of formula 1 where $R^1$ is methyl, $R^2$ is ethyl, $R^3$ and $R^4$ are each hydrogen, $R^5$ is said alkyl; $R^6$ is hydrogen, X and Z are each methoxy, Y is ethylene and Q is N. Especially preferred are those compounds where $R^5$ is methyl and R is 2-chlorophenyl, 2-chloro-3-fluorophenyl, 2,3-dichlorophenyl, 2-chloro-3-trifluoromethylphenyl, 2,3-difluorophenyl, 2-fluoro-3-chlorophenyl, 2-bromophenyl or 2-trifluoromethylphenyl.

Also preferred are compounds of formula 2 where $R^1$ is methyl and $R^2$ is ethyl. Especially preferred is the compound where $R^7$ is 2-chlorophenyl.

Also within the scope of the present invention is a pharmaceutical composition comprising a compound of formula 1 or 2 together with a pharmaceutically acceptable carrier or diluent, and a method for treating hypertension in a mammal comprising administering to said mammal an effective antihypertensive amount of a compound of formula 1 or 2.

The pharmaceutically acceptable salts of the compounds of the formulae 1 and 2 are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate and tartrate salts.

DETAILED DESCRIPTION OF THE INVENTION

The compounds of formula 1 are prpared by a number of different processes according to the invention.

(a) In one process the compounds of formula 1 wherein Q is N can be prepared by reacting a compound of the formula:

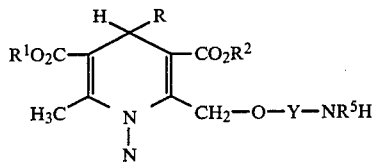

with a compound of the formula:

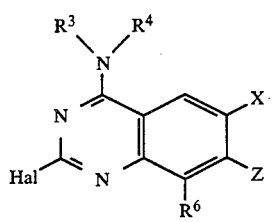

wherein R, $R^1$, $R^2$, $R^3$, $R^4$, $R^5$, $R^6$, X, Y and Z are as previously defined and Hal is a halogen atom, preferably chloro.

Similarly, this route is applicable to the synthesis of compounds of formula 2 as follows:

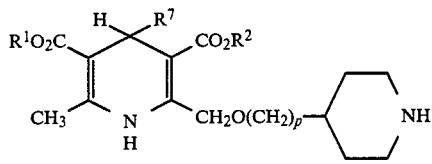

with a compound of the formula

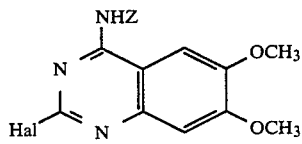

wherein $R^1$, $R^2$, $R^7$ and p are as previously defined and Hal is a halogen atom, preferably chloro.

The reaction is generally performed with more or less equimolar proportions of the reactants dissolved in a reaction-inert organic solvent. Suitable solvents are alkanols such as n-butanol and iso-amyl alcohol or dimethylsulphoxide. A base may also be present, to remove the acid formed in the reaction. A suitable example is 4-dimethylaminopyridine.

The reaction is typically achieved by heating the mixture at a temperature of from 100°–150° C. and is generally complete within a period of from 2 to 24 hours.

The starting materials of formula II and II$^1$ are prepared by conventional methods, for example by the Hantzsch synthesis as described in European Patent Application publication number 0089167. The quinazoline starting materials of formula III and III$^1$ generally known compounds prepared in accordance with published procedures, for example as described in British Patent number 1156973 and European Patent application publication number 100200.

(b) In an alternative process, compounds of the formula 1 wherein Q is N and $R^3$ and $R^4$ are both hydrogen can be prepared by reacting a compound of the formula:

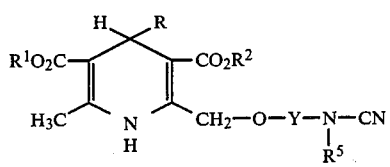

with a 2-amino-benzonitrile of the formula:

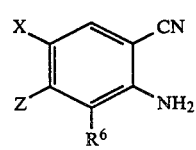

wherein R, $R^1$, $R^2$, $R^5$, $R^6$, X, Y and Z are as previously defined.

The reaction is conveniently performed by adding sodium hydride (2 equivalents) to a solution of the 2-amino-benzonitrile (V) in tetrahydrofuran. After a short while at a room temperature the dihydropyridine (IV) is added. The mixture is refluxed for one or two hours and the product isolated and purified by conventional methods.

In a similar manner, starting with the appropriate reagents compounds of formula 2 can also be prepared by this route.

The starting materials may be prepared from the corresponding 2-dialkylaminoalkoxymethyldihydropyridines, described for example in European patent application publication no. 60674, by reaction with cyanogen bromide.

(c) In a further process, compounds of the formula 1 wherein Q is CH and $R^3$ and $R^4$ are both hydrogen can be prepared by cyclising a compound of the formula:

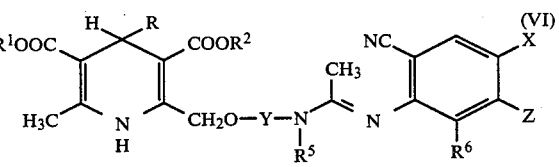

wherein R, $R^1$, $R^2$, $R^5$, $R^6$, X, Y and Z are as previously defined.

The cyclisation can be carried out using a Lewis acid, e.g. zinc chloide, or a base, e.g. lithium diisopropylamide. The reaction with zinc chloride is typically carried out by heating the reactants, preferably at reflux, in a suitable organic solvent, e.g. dimethylacetamide for up to about 4 hours. The reaction with lithium diisopropylamide is typically carried out at low temperature (e.g. −70° C.) in a suitable organic solvent, e.g. tetrahydrofuran, following which the reaction mixture is allowed to warm to room temperature. In some cases heating may be necessary to complete the reaction. The product can then be isolated and purified conventionally.

The starting materials of formula (VI) may be prepared from the appropriate 2-aminoalkoxymethyl-1,4-dihydropyridine and an appropriate substituted alkyl N-(2-cyanophenyl)acetimidate by conventional reactions, for example using the procedures described in European patent application publication number 100200.

The ability of the compounds to inhibit the moement of calcium into the cell is shown by their effectiveness in reducing the contraction of vascular tissue in vitro which is the consequence of calcium influx caused by a high extracellular concentration of potassium ions. The test is performed by mounting spirally cut strips of rat aorta with one end fixed and the other attached to a force transducer. The tissue is immersed in a bath of physiological saline solution containing calcium ions at a concentration of 2.5 millimolar and potassium ions at a concentration of 5.9 millimolar. Potassium chloride solution is added to the bath with a pipette to give a final potassium ion concentration of 45 millimolar. The change in tension caused by the resulting contraction of the tissue is noted. The bath is drained and refilled with fresh saline solution containing the particular compound under test. After 45 minutes, the procedure is repeated and the contraction again noted. The concentration of compound required to reduce the response by 50% is determined.

The in-vitro alpha$_1$ adrenoceptor binding affinity of the compounds is determined by measuring their ability to displace tritium labelled prazosin from a rat brain membrane preparation in accordance with the procedure of P. M. Greengrass and R. M. Bremner, European Journal of Pharmacology, 55, 323, 1979.

The in-vivo pharmacological profile of the compounds is assessed using chloralose anaesthetised cats measuring blood pressure, heart rate and contractions of the nictitating membrane. The compounds are injected intravenously. Alpha$_1$ adrenoceptor antagonist activity is assessed by measuring inhibition of responses of the nictitating membrane to electrical stimulation of he cervical sympathetic nerve. Calcium antagonist activity is assessed by measuring the reduction of pressor responses to injections of angiotensin II.

The antihypertensive activity of the compounds is evaluated after oral administration by measuring the fall in blood pressure in spontaneously hypertensive rats or renally hypertensive dogs.

For administration to man in the curative or prophylactic treatment of cardiac conditions and hypertension, oral dosages of the compounds will generally be in the range of from 2–200 mg daily for an average adult patient (70 kg). Thus for a typical adult patient, individual tablets or capsules contain from 1 to 20 mg of active compound, in a suitable pharmaceutically acceptable vehicle or carrier. Dosages for intravenous administration would typically be within the range 1 to 10 mg per single dose as required. In practice in physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formulae 1 and 2 can be administered alone, but will generally be administered in admixtue with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

Thus in a further aspect the invention provides a pharmaceutical composition comprising a compound of the formula 1 or 2, or a pharmaceutically acceptable salt thereof, together with a pharmaceutically acceptable diluent or carrier.

The invention also includes a compound of the formula 1 or 2, or a pharmaceutically acceptable salt thereof, for use in medicine, in particular in the prevention or treatment of cardiac conditions including ischaemic heart disease, angina and heart failure or for treatment of hypertension in a human being.

4-(2-Chlorophenyl)-3-ethoxycarbonyl-5-methoxycarbonyl-6-methyl-2-{2-[N-(4-amino-6,7-dimethoxyquijazol-2-yl)-N-methylamino]ethoxy-methyl}-1,4-dihydropyridine hemihydrate A mixture of 4-(2-chlorophenyl)-3-ethoxycarbonyl-5-methoxy-carbonyl-6-methyl-2-(2-N-methylaminoethoxymethyl)-1,4-dihydropyridine (9.0 g), 4-amino-2-chloro-6,7-dimethoxyquinazoline (5.1 g), 4-dimethylaminopyridine (3.0 g) and n-butanol (150 ml) was heated under reflux for 18 hours. The mixture was cooled and filtered and the filtrate was evaporated. The residue was chromatographed on silica gel. Elution with dichloromethane containing 1% methanol first gave impurity; increasing the methanol concentration to 5% then gave the pure product. The product fractions were combined and evaporated and the residue was triturated with di-isopropyl ether to give the title compound (1.49 g), m.p. 139°–141° C. Found: C, 58.60; H, 5.81; N, 11.09. $C_{31}H_{36}ClN_5O.\frac{1}{2}H_2O$ requires: C, 58.62; H, 5.87; N, 11.02%.

EXAMPLES 2–8

The following compounds were prepared by the method described in Example 1 using the appropriate quinazoline starting materials of formula III

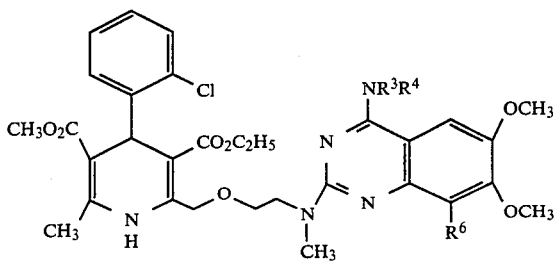

| Example No. | $R^3$ | $R^4$ | $R^6$ | m.p. (°C.) | Analysis % (Theoretical in brackets) | | |
|---|---|---|---|---|---|---|---|
| | | | | | C | H | N |
| 2 | $CH_3$ | H | H | — | 59.95 (60.04 | 6.05 5.98 | 10.81 10.94) |
| 3 | $CH_3$ | $CH_3$ | H | — | (a) | | |
| 4 | $C_2H_5$ | H | H | — | 60.80 (60.59 | 6.27 6.16 | 10.29 10.71) |
| 5 | $CH(CH_3)_2$ | H | H | 148 | 57.34 (57.95 | 5.96 6.15 | 10.09 9.94) |
| 6 | —$(CH_2)_4$— | | H | 209-212 | 58.62 (58.65 | 6.09 6.05 | 9.56 9.77) |
| 7 | H | H | $OCH_3$ | — | 58.74 (58.57 | 5.86 5.84 | 10.55 10.67) |
| 8 | $CH_3$ | $C_2H_5$ | H | 146-149(b) | 58.16 (57.95 | 5.86 6.15 | 9.48 9.94) |

(a)Characterised by $^1H$ NMR (CDCl$_3$): 1.17 (t, 3H, J = 7.1 Hz, CO$_2$CH$_2$Me); 2.04 (s, 3H, 6-Me); 3.20 (s, 6H, NMe$_2$); 3.31 (s, 3H, NMe); 3.57 (s, 3H, CO$_2$Me); ca 3.9 (m, 4H, OCH$_2$CH$_2$N); 3.91 (s, 3H, OMe), 3.96 (s, 3H, OMe); 4.03 (q, 2H, J = 7.1 Hz, CO$_2$CH$_2$Me); 4.70 (d, 1H) and 4.78 (d, 1H, J = 16.25 Hz), CH$_2$O; 5.34 (s, 1H 4-H); 6.92 (s, 1H) and 7.19 (s, 1H, quinazoline CH); 6.98-7.31 (m, aromatic CH and dihydropyridine NH).
(b)Hydrochloride salt

EXAMPLE 9

4-(2-Trifluoromethylphenyl)-3-ethoxycarbonyl-5-methoxycarbonyl-6-methyl-2-{2-[N-(4-amino-6,7-dimethoxyquinazol-2-yl)-N-methyl-amino)]ethoxymethyl}-1,4-dihydropyridine (i)
4-(2-Trifluoromethylphenyl)-3-ethoxycarbonyl-5-methoxycarbonyl-6-methyl-2-(2-N-benzyl-N-methylaminoethoxymethyl)-1,4-dihydropyridine A solution of 2-trifluoromethylbenzaldehyde (6.96 g) methyl 3-aminocrotonate (4.60 g) and ethyl 4-(2-N-benzyl-N-methylaminoethoxy)acetoacetate (11.72 g) in ethanol (80 ml) was heated under reflux with stirring for 20 hours and then evaporated. The residue was chromatographed on silica gel. Elution with a 4:1 mixture of petrol and chloroform first gave some impurity. Gradually increasing the concentration of chloroform gave more impurity and then finally the product was eluted with pure chloroform. The product fractions were combined and evaporated to give the title compound as a gum (6.0 g). Found: C, 64.34; H, 6.00; N, 4.79. $C_{29}H_{33}F_3N_2O_5$ requires: C, 63.72; H, 6.09; N, 5.13%.

(ii)
4-(2-Trifluoromethylphenyl)-3-ethoxycarbonyl-5-methoxycarbonyl-6-methyl-2-(2-N-methylaminoethoxymethyl)-1,4-dihydropyridine The above product (5.3 g) was dissolved in a mixture of methanol (100 ml) and concentrated hydrochloric acid (2 ml) and hydrogenated at 22° C. and 4 atm. pressure in the presence of 10% palladium on charcoal catalyst (0.5 g). When no further hydrogen was taken up, the catalyst was filtered off and the filtrate was evaporated. The residue was chromatographed on silica gel eluting with a 10:1 mixture of chloroform and methanol containing a trace of triethylamine. Evaporation of the product fractions gave the title compound (2.20 g), m.p. 106°-107° C. (from ethyl acetate/petrol). Found: C, 57.47; H, 5.93; N, 6.02. $C_{22}H_{27}F_3N_2O_5$ requires: C, 57.88; H, 5.96; N, 6.14%.

(iii)
4-(2-Trifluoromethylphenyl)-3-ethoxycarbonyl-5-methoxycarbonyl-6-methyl-2-2-[N-(4-amino-6,7-dimethoxyquinazol-2-yl)-N-methylamino]ethoxymethyl-1,4-dihydropyridine Treatment of the above compound with 4-amino-2-chloro-6,7-dimethoxyquinazoline by the method of Example 1 (7 hours reflux time) gave the title compound, m.p. 135°-136° C. (from di-isopropyl ether). Found: C, 58.23; H, 5.61; N, 10.52. $C_{32}H_{36}N_5O_7$ requires: C, 58.26; H, 5.50; N, 10.62%.

EXAMPLE 10-19

The following examples were prepared following the procedure of Example 8 using the appropriate dihydropyridine starting materials.

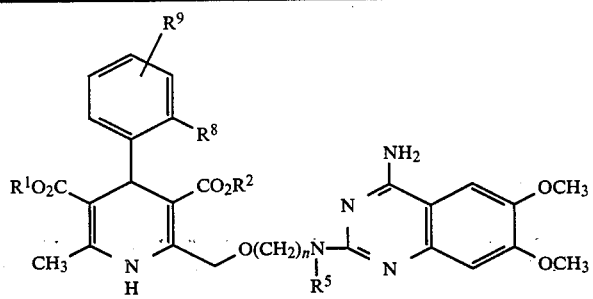

| Example No. | $R^1$ | $R^2$ | $R^5$ | $R^8$ | $R^9$ | n | m.p. °C. | Analysis % (Theoretical in brackets) | | |
|---|---|---|---|---|---|---|---|---|---|---|
| | | | | | | | | C | H | N |
| 10 | $CH_3$ | $C_2H_5$ | $CH_3$ | F | H | 2 | — | (a) | | |
| 11 | $CH_3$ | $C_2H_5$ | $CH_3$ | F | 3-F | 2 | 160 | 55.89 (56.06 | 5.65 5.46 | 10.36 10.54) |
| 12 | $CH_3$ | $C_2H_5$ | $CH_3$ | F | 3-Cl | 2 | — | 57.64 (57.80 | 5.55 5.48 | 10.66 10.87) |
| 13 | $CH_3$ | $C_2H_5$ | $CH_3$ | Cl | 3-F | 2 | — | (b) | | |

-continued

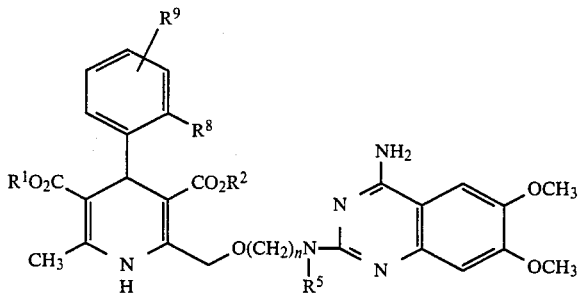

| Example No. | R¹ | R² | R⁵ | R⁸ | R⁹ | n | m.p. °C. | Analysis % (Theoretical in brackets) C | H | N |
|---|---|---|---|---|---|---|---|---|---|---|
| 14 | CH₃ | C₂H₅ | CH₃ | Cl | 6-F | 2 | — | 58.10 (57.80 | 5.66 4.58 | 10.72 10.87) |
| 15 | CH₃ | C₂H₅ | CH₃ | Cl | 3-CF₃ | 2 | 124–126 | 55.53 (55.37 | 5.17 5.08 | 9.83 10.09) |
| 16 | CH₃ | C₂H₅ | CH₃ | Cl | H | 3 | — | 60.27 (60.04 | 6.12 5.98 | 10.59 10.94) |
| 17 | CH₃ | CH₃ | CH₃ | Cl | H | 2 | — | 59.18 (58.87 | 5.87 5.60 | 11.63 11.44) |
| 18 | CH₂H₅ | CH₃ | CH₃ | Cl | H | 2 | — | (c) | | |
| 19 | CH₃ | C₂H₅ | C₂H₅ | Cl | H | 2 | — | (d) | | |

(a) ¹HNMR (CDCl₃): 1.17 (t, 3H, J = 7.2 Hz, CO₂CH₂Me); 2.08 (s, 3H, 6-Me); 3.27 (s, 3H, NMe); 3.57 (s, 3H, CO₂Me); ca 3.85 and ca 3.95 (m, 4H, OCH₂CH₂N); 3.93 (s, 3H, OMe); 3.96 (s, 3H, OMe); 4.02 (q, 2H, J = 7.2 Hz, CO₂CH₂Me); 4.74 (d, 1H) and 4.85 (d, 1H, J = 16.1 Hz), CH₂O; 5.10 (s, 2H, NH₂); 5.19 (s, 1H, 4-H); 6.75 (s, 1H) and 6.90 (s, 1H), quinazoline CH; 6.85–7.25 (m, 5H aromatic CH and dihydropyridine NH).
(b) ¹HNMR (CDCl₃): 1.17 (t, 3H, J = 7.1 Hz, CO₂CH₂Me); 2.07 (s, 3H, 6-Me); 3.27 (s, 3H, NMe); 3.57 (s, 3H, CO₂Me); ca 3.85 and ca 3.95 (m, 4H, OCH₂CH₂N); 3.91 (s, 3H, OMe); 3.95 (s, 3H, OMe); 4.04 (q, 2H, J = 7.1 Hz, CO₂CH₂Me); 4.75 (d, 1H) and 4.84 (d, 1H, J = 16.3 Hz), CH₂O; 5.14 (s, 2H, NH₂); 5.37 (s, 1H, 4-H), 6.68 (s, 1H) and 6.76 (s, 1H), quinazoline CH; 6.85–7.15 (m, 4H, aromatic CH and dihydropyridine NH).
(c) ¹HNMR (CDCl₃): 1.16 (t, 3H, J = 7.1 Hz, CO₂CH₂Me); 2.09 (s, 3H, 6-Me); 3.27 (s, 3H, NMe); 3.59 (s, 3H), CO₂Me); ca 3.83 and ca 4.0 (m, 4H, OCH₂CH₂N); 3.93 (s, 3H, OMe); 3.96 (s, 3H, OMe); 4.03 (q, 2H, J = 7.1 Hz, CO₂CH₂Me); 4.74 (d, 1H) and 4.84 (d, 1H, J = 16.2 Hz), CH₂O; 5.10 (s, 2H, NH₂); 5.35 (s, 1H, 4-H); 6.75 (s, 1H) and 6.90 (s, 1H), quinazoline CH; 6.98–7.35 (m, 5H, aromatic CH an dihydropyridine NH).
(d) ¹HNMR (CDCl₃): 1.18 (t, 3H, J = 7.1 Hz, CO₂CH₂Me); 1.23 (t, 3H, J = 7.0 Hz, NCH₂Me); 2.10 (s, 3H, 6-Me); 3.58 (s, 3H, CO₂Me); 3.76 (q, 2H, J = 7.0 Hz, NCH₂Me); ca 3.8–4.0 (m, 4H, OCH₂CH₂N; 3.92 (s, 3H, OMe); 3.96 (s, 3H, OMe); 4.04 (q, 2H, J = 7.1 Hz, CO₂CH₂Me); 4.78 (d, 1H) and 4.86 (d, 1H, J = 16.4 Hz) CH₂O; 5.12 (s, 2H, NH₂), 5.35 (s, 1H, 4-H); 6.75 (s, 1H) and 6.88 (s, 1H) quinazoline CH; 6.98–7.35 (m, 5H, aromatic CH and dihydropyridine NH).

EXAMPLE 20

4-(2-Bromophenyl)-3-ethoxycarbonyl-5-methoxycarbonyl-6-methyl-2-{2-[N-(4-amino-6,7-dimethoxyquinazol-2-yl)-N-methylamino]ethoxymethyl}-1,4-dihydropyridine (i)
4-(2-Bromophenyl)-3-ethoxycarbonyl-5-methoxycarbonyl-6-methyl-2-(2-N,N-dimethylaminoethoxymethyl)-1,4-dihydropyridine 2-Bromobenzaldehyde (5.60 g) was added dropwise to a stirred solution of ethyl 4-(2-dimethylaminoethoxy)acetoacetate (6.52 g) and the solution was warmed to 50° C. for 5 minutes and then cooled. Methyl 3-aminocrotonate (3.46 g) was added and the solution was heated under reflux for 20 hours and then evaporated. The residue was chromatographed on silica gel. The column was eluted with a 1:1 mixture of petrol and chloroform, gradually increasing the concentration of CHCl₃ to remove a small amount of by-product. The product was eluted with a 20:1 mixture of chloroform and methanol. The product fractions were combined and evaporated to give the title compound (3.2 g), m.p. 109°–110° C. (from ethyl acetate/hexane). Found: C, 54.75; H, 6.08; N, 5.88. C₂₂H₂₉BrN₂O₅ requires: C, 54.89; H, 6.07; N, 5.82%.

(ii)
4-(2-Bromophenyl)-3-ethoxycarbonyl-5-methoxycarbonyl-6-methyl-2-(2-N-methylaminoethoxymethyl)-1,4-dihydropyridine 2,2,2-Trichloroethyl chloroformate (1.20 g) was added dropwise to a stirred solution of the above product (2.60 g) in dry toluene (30 ml) at 5° C. and the resulting solution was heated under reflux for 18 hours. It was cooled and 2N hydrochloric acid (30 ml) was added. The mixture was stirred for 10 minutes, diluted with diethylether and the organic phase was separated, washed with water and dried over sodium sulphate. Evaporaton of the solvent gave a gum which was dissolved in 90% acetic acid (35 ml). The solution was cooled to 0° C. and zinc dust (4.50 g) was added portionwise with stirring. The mixture was stirred at room temperature for 20 hours and then filtered. The filtrate was evaporated and the residue was partitioned between ethyl acetate and water. The organic layer was separated, washed with concentrated ammonia solution, water and dried over sodium sulphate. Evaporation of the solvent gave a gum which was chromatographed on silica gel. Elution with a 50:1 mixture of chloroform and methanol initially gave some impurity. When the product started to appear the ratio of chloroform:methanol was changed to 10:1 and finally a trace of triethylamine was included to elute all the product. The product fractions were combined and evaporated to give the tiele compound (0.80 g), m.p. 88°–89° C.

(from ethyl acetate/hexane). Found: C, 53.89; H, 5.83; N, 5.73. $C_{21}H_{27}N_2O_5$ requires: C, 53.96; H, 5.82; N, 6.00%.

(iii)
4-(2-Bromophenyl)-3-ethoxycarbonyl-5-methoxycarbonyl-6-methyl-2-{2-[N-(4-amino-6,7-dimethoxyquinazol-2-yl)-N-methylamino]ethoxymethyl}-1,4-dihydropyridine Treatment of the above compound with 4-amino-2-chloro-6,7-dimethoxyquinazoline according to the method of Example 1 (8 hours reflux time) gave the title compound as an amorphous glass. Found C, 55.35; H, 5.41; N, 9.70. $C_{31}H_{36}BrN_5O_7$ requires: C, 55.52; H, 5.41; N, 10.45%.

EXAMPLE 21

4-(2,3-Dichlorophenyl)-3-ethoxycarbonyl-5-methoxycarbonyl-6-methyl-2-{2-[N-(4-amino-6,7-dimethoxyquinazol-2-yl)-N-methylamino]ethoxymethyl}-1,4-dihydropyridine (i)
4-(2,3-Dichlorophenyl)-3-ethoxycarbonyl-5-methoxycarbonyl-6-methyl-2-[2-N,N-dimethylaminoethoxymethyl]-1,4-dihydropyridine Reaction of 2,3-dichlorobenzaldehyde with ethyl 4-(2-dimethylaminoethoxy)acetoacetate and ethyl 3-aminocrotonate by the method of Example 20(i) gave the title compound, m.p. 101°–103° C. Found: C, 55.93; H, 5.76; N, 6.20. $C_{22}H_{28}Cl_2N_2O_5$ requires: C, 56.05; H, 5.99; N, 5.94%.

(ii)
4-(2,3-Dichlorophenyl)-3-ethoxycarbonyl-5-methoxycarbonyl-6-methyl-2-[2-N-methylaminoethoxymethyl]-1,4-dihydropyridine Treatment of the above compound with 2,2,2-trichloroethyl chloroformate followed by zinc dust in acetic acid according to the method of Example 20(ii) gave the title compound which was used directly in the next stage.

(iii)
4-(2,3-Dichlorophenyl)-3-ethoxycarbonyl-5-methoxycarbonyl-6-methyl-2-{2-[N-(4-amino-6,7-dimethoxyquinazol-2-yl-N-methylamino]ethoxymethyl}-1,4-dihydropyridine Treatment of the above compound with 4-amino-2-chloro-6,7-dimethoxyquinazoline by the method of Example 1 gave the title compound as an amorphous glass, (CDCl$_3$): 1.17 (t, 3H, J=7.1 Hz, CO$_2$CH$_2$Me); 2.05 (s, 3H, 6-Me); 3.28 (s, 3H, NMe); 3.57 (s, 3H, CO$_2$Me), ca 3.85 (m, 2H) and ca 3.95 (m, 2H), OCH$_2$CH$_2$N; 3.92 (s, 3H, OMe); 3.95 (s, 3H, OMe); 4.05 (q, 2H, J=7.1 Hz, CO$_2$CH$_2$Me); 4.74 (d, 1H) and 4.82 (d, 1H, J=16.2 Hz), CH$_2$O; 5.10 (s, 2H, NH$_2$); 5.40 (s, 1H, 4-H); 6.74 (s, 1H) and 6.89 (s, 1H, quinazoline CH); 6.95–7.25 (m aromatic CH); 7.06 (s, 1H, NH).

EXAMPLE 22

1-(4-Amino-6,7-dimethoxyquinazol-2-yl-4-[4-(2-chloro-3-trifluoromethylphenyl)-3-ethoxycarbonyl-5-methoxycarbonyl-6-methyl-1,4-dihydropyrid-2-yl-methoxy]-piperidine (i) Ethyl 4-(1-methylpiperid-4-yloxy)acetoacetate Sodium hydride (5.0 g of 50% dispersion in mineral oil) was added portionwise to a stirred solution of 4-hydroxy-1-methyl-piperidine (11.5 g) in dry dimethylformamide (80 ml). The mixture was stirred at room temperature for 1 hour and then cooled to 10° C. A solution of ethyl 4-chloroacetoacetate (8.2 g) in dry dimethylformamide (20 ml) was added dropwise with stirring and stirring was continued for a further 20 hours at room temperature. Ethanol (10 ml) was added and the solution was evaporated to dryness. The residue was partitioned between dichloromethane and dilute hydrochloric acid. The organic layer was separated, dried over sodium sulphate and evaporated to given an oil which was partitioned between acetonitrile and petrol to remove mineral oil. The acetonitrile extract was evaporated to give the title compound as an oil (10.3 g) which was used without further purification.

(ii)
1-Methyl-4-[4-(2-chloro-3-trifluoromethylphenyl)-3-ethoxycarbonyl-5-methoxycarbonyl-6-methyl-1,4-dihydropyrid-2-yl-methoxy]piperidine A mixture of the above product (9.72 g), 2-chloro-3-trifluoromethylbenzaldehyde (8.34 g), methyl 3-aminocrotonate (4.61 g), acetic acid (4 ml) and ethanol (30 ml) was heated under reflux for 6 hours and then evaporated. The residue was partitioned between toluene and 2N hydrochloric acid. The acidic layer was separated and the toluene layer was washed with 2N hydrochloric acid. The combined acidic layers were extracted several times with dichloromethane. The organic extracts were combined and washed well with ammoniacal brine, dried over sodium sulphate and evaporated. The residual oil was chromatographed on silica gel. Elution with a 10:1 mixture of chloroform and methanol gave the product (9.0 g), m.p. 180°–181° C. (from chloroform/petrol). Found: C, 56.40; H, 5.67; N, 5.17. $C_{25}H_{30}ClF_3N_2O_5$ requires: C, 56.55; H, 5.70; N, 5.28%.

(iii)
4-[4-(2-chloro-3-trifluoromethylphenyl)-3-ethoxycarbonyl-5-methoxycarbonyl-6-methyl-1,4-dihydropyrid-2-yl-methoxy]piperidine Treatment of the above product with 2,2,2-trichloroethyl chloroformate followed by zinc and acetic acid according to the method of Example 2(ii) gave the title compound, m.p. 162°–163° C. (from ethyl acetate/petrol). Found: C, 55.78; H, 5.50; N, 5.37. $C_{24}H_{28}ClF_3N_2O_5$ requires: C, 55.76; H, 5.46; N, 5.42%.

(iv)
1-(4-Amino-6,7-dimethoxyquinazol-2-yl)-4-[4-(2-chloro-3-trifluoromethylphenyl)-3-ethoxycarbonyl-5-methoxycarbonyl-6-methyl-1,4-dihydropyrid-2-yl-methoxy]piperidine Treatment of the above product with 4-amino-2-chloro-6,7-dimethoxyquinazoline according to the method of Example 1 gave the title compound, m.p. 145°–146° C. (from ether). Found: C, 56.77; H, 5.26; N, 9.80. $C_{34}H_{37}ClF_3H_5O_7$ requires: C, 56.70; H, 5.18; N, 9.73%.

EXAMPLE 23

1-(4-Amino-6,7-dimethoxyquinazol-2-yl)-4-[4-(2-chlorophenyl)-3-ethoxycarbonyl-5-methoxycarbonyl-6-methyl-1,4-dihydropyrid-2-yl-methoxy]piperidine (i)
1-Methyl-4-[4-(2-chlorophenyl)-3-ethoxycarbonyl-5-methoxycarbonyl-6-methyl-1,4-dihydropyrid-2-yl-methoxy]piperidine Reaction of 2-chlorobenzaldehyde, ethyl 4-(1-methylpiperid-4-yloxy)acetoacetate and methyl 3-aminocrotonate according to the method of Example 22(ii) gave the title compound which was used directly in the next stage.

(ii)
4-[4-(2-chlorophenyl)-3-ethoxycarbonyl-5-methoxycarbonyl-6-methyl-1,4-dihydropyrid-2-yl-methoxy]piperidine Treatment of the above intermediate with 2,2,2-trichloroethyl chloroformate followed by zinc and acetic acid according to the method of Example 20(ii) gave the title compound as a gum. A portion was converted to the fumarate hemihydrate, m.p. 175°–176° C. (from ethyl acetate/methanol). Found: C, 56.26; H, 5.87; N, 4.87. $C_{23}H_{29}ClN_2O_5 \cdot C_4H_4O_4 \cdot \frac{1}{2}H_2O$ requires: C, 56.49; H, 5.97; N, 4.88%.

(iii)
1-(4-Amino-6,7-dimethoxyquinazol-2-yl)-4-[4-(2-chlorophenyl)-3-ethoxycarbonyl-5-methoxycarbonyl-6-methyl-1,4-dihydropyrid-2-yl-methoxy]piperidine Treatment of the above intermediate with 4-amino-2-chloro-6,7-dimethoxyquinazoline according to the method of Example 1 gave the title compound as an amorphous glass, (CDCl$_3$) 1.20 (t, 3H, J=7.1 Hz, CO$_2$CH$_2$Me); 1.6–1.75 (m, 2H, piperidine CH); 2.0–2.15 (m, 2H, piperidine CH); 2.33 (s, 3H, 6-Me); 3.25–3.4 (m, 2H, piperidine CH); 3.62 (s, 3H, CO$_2$Me); ca 3.7 (m, 1H, piperidine 4-H); 3.93 (s, 3H, OMe); 3.98 (s, 3H, OMe); 4.06 (q, 2H, J=7.1 Hz, CO$_2$CH$_2$Me); 4.4–4.55 (m, 2H, piperidine CH); 4.75 (d, 1H) and 4.84 (d, 1H, J=16.3 Hz), CH$_2$O; 5.11 (s, 2H, NH$_2$); 5.42 (s, 1H, 4-H); 6.78 (s, 1H) and 6.92 (s, 1H, quinazoline CH); 7.0–7.4 (m, aromatic CH and dihydropyridine NH).

EXAMPLE 24

1-(4-Amino-6,7-dimethoxyquinazol-2-yl)-4-[4-(2-chlorophenyl)-3-ethoxycarbonyl-5-methoxycarbonyl-6-methyl-1,4-dihydropyrid-2-yl-methoxymethyl]piperidine (i) Ethyl 4-(1-benzylpiperid-4-ylmethoxy)acetoacetate Treatment of ethyl 4-chloroacetoacetate with 1-benzylpiperidine-4-methanol according to the method of Example 22(i) gave the title compound as an oil which was used directly in the next step.

(ii)
1-Benzyl-4-[4-(2-chlorophenyl)-3-ethoxycarbonyl-5-methoxycarbonyl-6-methyl-1,4-dihydropyrid-2-yl-methoxymethyl]piperidine Treatment of the above intermediate with 2-chlorobenzyaldehyde and methyl 3-aminocrotonate according to the method of Example 9(i) gave the title product as an oil. Found: C, 67.13; H, 6.71; N, 5.09. $C_{31}H_{37}ClN_2O_5$ requires: C, 67.32; H, 6.74; N, 5.07%.

(iii)
4-[4-(2-Chlorophenyl)-3-ethoxycarbonyl-5-methoxycarbonyl-6-methyl-1,4-dihydropyrid-2-yl-methoxymethyl]piperidine Hydrogenation of the above product according to the method of Example 9(ii) gave the title compound as an oil which was used directly in the next step.

1-(4-Amino-6,7-dimethoxyquinazol-2-yl)-4-[4-(2-chlorophenyl)-3-ethoxycarbonyl-5-methoxycarbonyl-6-methyl-1,-4-dihydropyrid-2-yl-methoxymethylmethyl]-piperidine Treatment of the above intermediate with 4-amino-2-chloro-6,7-dimethoxyquinazoline by the method of Example 1 (3 hours reflux time) gave the title compound as an amorphous solid. Found: C, 61.19; H, 6.11; N, 10.09. $C_{34}H_{40}ClN_5O_7$ requires: C, 61.30; H, 6.05; N, 10.51%.

EXAMPLE 25

4-(2-Chlorophenyl)-3-ethoxycarbonyl-5-methoxycarbonyl--6-methyl-2-{2-[N-(4-aminoquinazol-2-yl)-N-methylamino]ethoxymethyl}-1,4-dihydropyridine hydrochloride sesquihydrate (i)
4-(2-Chlorophenyl)-3-ethoxycarbonyl-5-methoxycarbonyl-6-methyl-2-[2-(N-cyano-N-methyl)aminoethoxymethyl]-1,4-dihydropyridine A solution of 4-(2-chlorophenyl)-3-ethoxycarbonyl-5-methoxycarbonyl-6-methyl-2-(2-dimethylaminoethoxy)methyl-1,4-dihydroypyeisinw (10.0 g) in chloroform (100 ml.) was added dropwise to a stirred solution of cyanogen bromide (2.43 g) in chloroformm (20 ml) at room temperature. The solution was stirred for 1½ hours and then washed with dilute hydrochloric acid. The aqueous layer was washed with chloroform and the organic layers were combined, washed with water and dried over sodium sulphate. Evaporation of the solvent gave a solid which was chromatographed on silica gel. Elution with chloroform/petroleum ether (b.p. 40°–60° C.) (1:1) gradually increasing the ratio to 4:1 gave the title compound (6.79 g), m.p. 150°–151° C. (from ethyl acetate). Found: C, 59.25; H, 5.71; N, 9.39. $C_{22}H_{26}ClN_3O_5$ requires: C, 58.99; H, 5.85; N, 9.38%.

(ii)
4-(2-Chlorophenyl)-3-ethoxycarbonyl-5-methoxycarbonyl-6-methyl-2-{2-[N-(3-aminoquinazol-2-yl)-N-methylamino]ethoxymethyl}-1,4-dihydropyridine hydrochloride sesquihydrate Sodium hydride (118 mg. of 50% dispersion in mineral oil) was added to a stirred solution of anthranilonitrile (132 mg.) in dry tetrahydrofuran (10 ml) and the mixture was stirred at room temperature for 45 minutes. A solution of the product from (i) above (500 mg.) in dry tetrahydrofuran was added dropwise with stirring. The mixture was heated under reflux for 1½ hours, cooled and ethanol (1 ml.) was added. The solution was evaporated and the residue was chromatographed on silica gel. Elution with chloroform/petroleum ether (b.p. 40°–60° C.) (1:1) first gave mineral oil followed by product was a gum (240 mg.). The gum was dissolved in diethyl ether and an excess of ethereal hydrogen chloride was added. The solid was filtered off and dried go give the title compound as the hydrochloride sesquihydrate, m.p. ca. 120° C. (decomp.) Found: C, 55.48; H, 5.49; N, 10.92. $C_{29}H_{32}ClN_5O_5.HCl.1.5\ H_2O$ requires: C, 55.37; H, 5.61; N, 11.13%.

EXAMPLE 26

4-(2-Chlorophenyl)-3-ethoxycarbonyl-5-methoxycarbonyl-6-methyl-2-{2-[N-(4-amino-6-methoxyquinazol-2-yl)-N-methylamino]ethoxymethyl}-1,4-dihydropyridine Treatment of 4-(2-chlorophenyl)-3-ethoxycarbonyl-6-methoxycarbonyl-6-methyl-2-[2-N-cyano-N-methyl-)aminoethoxymethyl]-1,4-dihydropyridine with 2-amino-5-methoxybenzonitrile according to the method of Example 25(ii) gave the title compound as a gum, (CDCl$_3$): 1.18 (t, 3H, J=7.1 Hz, CO$_2$CH$_2$Me); 2.05 (s, 3H, 6-Me); 3.28 (s, 3H, NMe); 3.57 (s, 3H, CO$_2$Me); 3.79–3.92 (m, 6H, OCH$_2$CH$_2$N); 3.85 (s, 3H, OMe), 4.04 (q, 2H, J=7.1 Hz, CO$_2$CH$_2$Me); 4.75 (d, 1H) and 4.85 (d, 1H, J=16.2 Hz), CH$_2$O; 5.22 (s, 2H, NH$_2$); 5.34 (s, 1H, 4-H); 6.81 (d, 1H, J=2.6 Hz, quinazoline H-5); 6.97–7.30 (m, 5H, aromatic CH and dihydropyridine NH); 7.45 (d, 1H, J=8.5 Hz, quinazoline H-8).

EXAMPLE 27

4-(2-Chlorophenyl)-3-ethoxycarbonyl-5-methoxycarbonyl-6-methyl-2-{2-[N-(4-amino-7-methoxyquinazol-2-yl)-N-methylamino]ethoxy-methyl}-1,4-dihydropyridine Treatment of 4-(2-chlorophenyl)-3-ethoxycarbonyl-6-methoxycarbonyl-6-methyl-2-[2-(N-cyano-N-methyl-)aminoethoxymethyl]-1,4-dihydropyridine with 2-amino-4-methoxybenzonitrile according to the method of Example 25(ii) gave the title compound as a gum, CDCl$_3$): 1.20 (t, 3H, J=7.1 Hz, CO$_2$CH$_2$Me), 2.08 (s, 3H, 6-Me); 3.31 (s, 3H, NMe); 3.60 (s, 3H, CO$_2$Me); ca 3.8–4.1 (m, 4H, OCH$_2$CH$_2$N), 3.89 (s, 3H, OMe); 4.06 (q, 2H, J=7.1 Hz, CO$_2$CH$_2$Me); 4.77 (d, 1H) and 4.86 (d, 1H, J=16.2 Hz), CH$_2$O; 5.22 (s, 2H, NH$_2$); 5.37 (s, 1H, 4-H); 6.70–7.42 (8H, aromatic CH and dihydropyridine NH).

EXAMPLE 28

4-(2-Chlorothien-3-yl)-3-ethoxycarbonyl-5-methoxycarbonyl-6-methyl-2-{2-[N-(4-amino-6,7-dimethoxyquinazol-2-yl)-N-methyl-amino]-ethoxy}methyl-1,4-dihydropyridine (i)

4-(2-Chlorothien-3-yl)-3-ethoxycarboyl-5-methoxycarbonyl-6-methyl-2-(2-dimethylaminoethoxymethyl)-1,4-dihydropyridine Reaction of 2-chlorothiophene-3-carboxaldehyde with ethyl 4-(2-dimethylaminoethoxy)acetoacetate and methyl 3-aminocrotonate in ethanol according to the method of Example 9(i) gave the title compound, m.p. 110°–112° C. (from ethyl acetate/petrol b.p. 60°–80° C.). Found: C, 53.72; H, 6.26; N, 6.09. $C_{20}H_{27}ClN_2O_5S$ requires: C, 54.22; H, 6.14; N, 6.32%.

(ii)

4-(2-Chlorothien-3-yl)-3-ethoxycarbonyl-5-ethoxycarbonyl-6-methyl-2-[2-(N-cyano-N-methyl)aminoethoxymethyl]-1,4-dihydropyridine Treatment of the above intermediate with cyanogen bromide according to the method of Example 25(i) gave the title compound, m.p. 151°–152° C. (from ethyl acetate). Found: C, 52.83; H, 5.32; N, 8.95. $C_{20}H_{24}ClN_3O_5S$ requires: C, 52.91; H, 5.32; N, 9.26%.

(iii)

(4-(2-Chlorothien-3-yl)-3-ethoxycarbonyl-5-methoxycarbonyl-6-methyl-2-{2-[N-(2-(4-amino-6,7-dimethoxyquinazol-2-yl)-N-methylamino]ethoxymethyl}-1,4-dihydropyridine Treatment of the above intermediate with 2-amino-4,5-dimethoxybenzonitrile according to the method of Example 25(ii) gave the title compound as an amorphous solid, (CDCl$_3$): 1.25 (t, 3H, J=7.1 Hz, CO$_2$CH$_2$Me); 2.09 (s, 3H, 6-Me); 3.29 (s, 3H, NMe), 3.64 (s, 3H, CO$_2$Me): ca 3.85 and ca 3.95 (m, 4H, OCH$_2$CH$_2$N); 3.95 (s, 3H, OMe); 3.98 (s, 3H, OMe), 4.09 (q, 2H, J=7.1 Hz, CO$_2$CH$_2$Me); 4.77 (d, 1H) and 4.85 (d, 1H, J=16.2 Hz), CH$_2$O; 5.12 (br s, 3H, NH$_2$ and 4-H), 6.68 (d, 1H, J=5.8 Hz, thiophene H-4), 6.80 (d, 1H, J=5.8 Hz, thiophene H-5), 6.76 (s, 1H) and 6.91 (s,1H), quinazoline CH; 7.08 (s, 1H, NH).

EXAMPLE 29

4-(2-Chlorophenyl)-3-ethoxycarbonyl-5-methoxycarbonyl-6-methyl-2-{2-[N-(4-amino-6,7-dimethoxyquinazol-2-yl)-N-(2-hydroxyethyl)-amino]ethoxymethyl}-1,4-dihydropyridine (i)

4-(2-Chlorophenyl)-3-ethoxycarbonyl-5-methoxycarbonyl-6-methyl-2-{2-[N-(4-amino-6,7-dimethoxyquinazol-2-yl)-N-(2-hydroxyethyl)-amino]ethoxymethyl}-1,4-dihydropyridine A mixture of 4-(2-chlorophenyl)-3-ethoxycarbonyl-5-methoxycarbonyl-6-methyl-2-(2-methylamino-ethoxymethyl)-1,4-dihydropyridine (3.80 g.), 2-benzyloxyethyl chloride (1.54 g.), sodium iodide (1.35 g.) and anhydrous sodium carbonate (0.95 g.) in acetone (80 ml.) was heated under reflux with stirring for 18 hours. The mixture was cooled, filtered and the residue was washed with acetone. The filtrate and wasings were evaporated and the residue was chromatographed on silica gel. Elution with chloroform gave the product as an oil (2.30 g.). Found: C, 64.85; H, 6.91; N, 5.29. $C_{30}H_{37}ClN_2O_6$ requires: C, 64.68; H, 6.70; N, 5.03%.

(ii)

4-(2-Chlorophenyl)-3-ethoxycarbonyl-5-methoxycarbonyl-2-{2-[N-cyano-N-(2-benzyloxyethyl)-amino]ethoxymethyl}-1,4-dihydropyridine Treatment of the above intermediate with cyanogen bromide according to the method of Example 25(i) gave the title product, m.p. 102°–103° C. Found: C, 63.56; H, 6.09; N, 7.63. $C_{30}H_{34}ClN_3O_6$ requires: C, 63.43; H, 6.03; N, 7.40%.

(iii)

4-(2-Chlorophenyl)-3-ethoxycarbonyl-5-methoxycarboyl-6-methyl-2-{2-[N-(4-amino-6,7-dimethoxyquinazol-2-yl)-N-(2-benzyloxyethyl)amino]ethoxymethyl}-1,4-dihydropyridine Treatment of the above intermediate with 2-amino-4,5-dimethoxybenzonitrile according to the method of Example 25(ii) gave the title product as an amorphous solid. Found: C, 62.66; H, 6.11; N, 8.72. $C_{39}H_{44}ClN_5O_8$ requires: C, 62.77; H, 5.94; N, 9.39%.

(iv) 4-(2-Chlorophenyl)-3-ethoxycarbonyl-5-methoxycarbonyl-6-methyl-2-{2-[N-(4-amino-6,7-dimethoxyquinazol-2-yl)-N-(2-hydroxyethyl)amino]ethoxymethyl}-1,4-dihydropyridine A solution of the above intermediate (0.18 g.) in ethanol (30 ml.) and concentrated hydrochloric acid (0.2 ml.) was hydrogenated at 22° C. and 4 atm. pressure in the presence of 10% palladium on carbon (18 mg.). When no further hydrogen was absorbed the solution was filtered and evaporated. The residue was partitioned between sodium bicarbonate solution and ethyl acetate. The aqueous layer was washed with ethyl acetate and the combined organic layers were dried over sodium sulphate and evaporated. The residue was chromatographed on silica gel. Elution with chloroform/hexane (1:1) first gave impurity; further elution with chloroform followed by chloroform/methanol (20:1) gave the title compound as an amorphous solid (0.08 g.). Found: C, 58.29; H, 6.31; N, 9.88. $C_{32}H_{38}ClN_5O_8$ requires: C, 58.57; H, 5.84; N, 10.67%.

EXAMPLE 30

4-(2-Chlorophenyl)-3-ethoxycarbonyl-5-methoxycarbonyl-6-methyl-2-{2-[N-(4-aminoquinol-2-yl)-N-methylamino]ethoxymethyl}-1,4-dihydropyridine

(i) N-{2-[4-(2-Chlorophenyl)-3-ethoxycarbonyl-5-methoxycarbonyl-6-methyl-1,4-dihydropyrid-2-yl]methoxyethyl}-N-methyl-N'-(2-cyanophenyl)acetamidine A mixture of 4-(2-chlorophenyl)-3-ethoxycarbonyl-5-methoxycarbonyl-6-methyl-2-(2-methylaminoethoxymethyl)-1,4-dihydropyridine (2.5 g.), ethyl N-(2-cyanophenyl)acetimidate (1.1 g.) and p-toluenesulphonic acid (0.1 g.) was heated at 150° C. for 4 hours, cooled, and then dissolved in chloroform. The solution was washed with sodium bicarbonate solution, water and dried over sodium sulphate. Evaporation of the solvent gave an oil which was chromatographed on silica gel. Elution with chloroform/hexane (1:1) gave the product as an oil (0.95 g.) which was used directly in the next stage.

(ii) 4-(2-Chlorophenyl)-3-ethoxycarabonyl-5-methoxycarbonyl-6-methyl-2-{2-[N-(4-aminoquinol-2-yl)-N-methylamino]ethoxymethyl}-1,4-dihydropyridine n-Butyllithium (4.5 ml. of 1.6M solution in hexane) was added dropwise to a stirred solution of di-isopropylamine (0.72 g.) in dry tetrahydrofuran (15 ml.) at −70° C. and the solution was stirred at −70° C. for 10 minutes. A solution of the above intermediate (0.5 g.) in dry tetrahydrofuran (10 ml.) was added dropwise with stirring over 5 minutes. The resulting solution was stirred at −70° C. for 3½ hours and then at room temperature for 18 hours. The solution was poured into water and the mixture was extracted several times with chloroform. The combined extracts were washed with water, dried over sodium sulphate and evaporated. The residue was chromatographed on silica gel. Elution with chloroform/hexane (1:1) gave some starting material; further elution with chloroform and finally with chloroform/methanol (10:1) gave the title compound as an amorphous solid (0.25 g.). Found: C, 63.31; H, 6.07; N, 10.01. $C_{30}H_{33}ClN_4O_5$ requires: C, 63.76; H, 5.88; N, 9.92%.

PREPARATION 1

The following starting materials of formula II were prepared as described in Example 9(i) and 9(ii). The products were used for Examples 9–19.

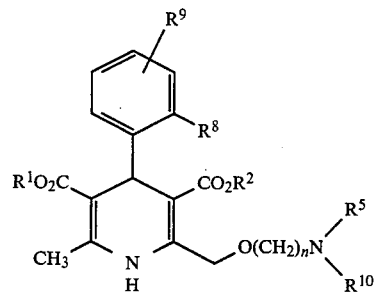

| | | | | | | | | Analysis % (Theoretical in Brackets) | | |
|---|---|---|---|---|---|---|---|---|---|---|
| $R^1$ | $R^2$ | $R^5$ | $R^8$ | $R^9$ | $R^{10}$ | n | m.p. °C. | C | H | H |
| $CH_3$ | $C_2H_5$ | $CH_3$ | F | H | $CH_2Ph$ | 2 | 91–92 | 67.91 | 6.73 | 5.56 |
| | | | | | | | | (67.72 | 6.70 | 5.64) |
| $CH_3$ | $C_2H_5$ | $CH_3$ | F | H | H | 2 | — | USED WITHOUT CHARACTERIZATION | | |
| $CH_3$ | $C_2H_5$ | $CH_3$ | F | 3-F | $CH_2Ph$ | 2 | 73–74 | 65.18 | 6.20 | 5.13 |
| | | | | | | | | (65.35 | 6.27 | 5.44) |
| $CH_3$ | $C_2H_5$ | $CH_3$ | F | 3-F | H | 2 | 168–171 | 54.55 | 5.79 | 6.17 |
| | | | | | | | | (54.72 | 5.90 | 6.08) |
| $CH_3$ | $C_2H_5$ | $CH_3$ | F | 3-Cl | $CH_2Ph$ | 2 | — | 63.71 | 6.15 | 4.92 |
| | | | | | | | | (63.33 | 6.08 | 5.28) |
| $CH_3$ | $C_2H_5$ | $CH_3$ | F | 3-Cl | H | 2 | 188–189 | 52.80 | 5.73 | 5.92 |
| | | | | | | | | (52.83 | 5.70 | 5.87) |
| $CH_3$ | $C_2H_5$ | $CH_3$ | Cl | 3-F | $CH_2Ph$ | 2 | 82–83 | 62.72 | 6.12 | 5.12 |
| | | | | | | | | (63.33 | 6.08 | 5.28) |
| $CH_3$ | $C_2H_5$ | $CH_3$ | Cl | 3-F | H | 2 | 101.102 | 56.97 | 5.95 | 6.12 |
| | | | | | | | | (57.20 | 5.94 | 6.36) |
| $CH_3$ | $C_2H_5$ | $CH_3$ | Cl | 6-F | $CH_2Ph$ | 2 | 87.88 | 63.63 | 6.06 | 5.44 |
| | | | | | | | | (63.33 | 6.08 | 5.28) |

-continued

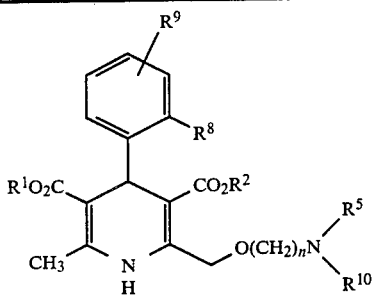

| R¹ | R² | R⁵ | R⁸ | R⁹ | R¹⁰ | n | m.p. °C | C | H | H |
|---|---|---|---|---|---|---|---|---|---|---|
| | | | | | | | | \multicolumn{3}{c}{Analysis % (Theoretical in Brackets)} |
| $CH_3$ | $C_2H_5$ | $CH_3$ | Cl | 6-F | H | 2 | 165–166[a] | 53.22 (52.83) | 5.81 5.70 | 5.83 5.87 |
| $CH_3$ | $C_2H_5$ | $CH_3$ | Cl | 3-$CF_3$ | $CH_2Ph$ | 2 | 145–148 | 56.21 (56.40) | 5.50 5.39 | 4.62 4.54) |
| $CH_3$ | $C_2H_5$ | $CH_3$ | Cl | 3-$CF_3$ | H | 2 | 184–187 | 49.97 (50.10) | 5.22 5.16 | 5.31 5.31) |
| [d]$CH_3$ | $C_2H_5$ | $CH_3$ | Cl | H | $CH_2Ph$ | 3 | — | \multicolumn{3}{c}{USED WITHOUT CHARACTERIZATION} |
| $CH_3$ | $C_2H_5$ | $CH_3$ | Cl | H | H | 3 | — | \multicolumn{3}{c}{USED WITHOUT CHARACTERIZATION} |
| [d]$CH_3$ | $CH_3$ | $CH_3$ | Cl | H | $CH_2Ph$ | 2 | — | \multicolumn{3}{c}{USED WITHOUT CHARACTERIZATION} |
| $CH_3$ | $CH_3$ | $CH_3$ | Cl | H | H | 2 | 175–177[a] | 53.60 (53.94) | 5.82 5.88 | 6.21 6.29) |
| [d]$C_2H_5$ | $CH_3$ | $CH_3$ | Cl | H | $CH_2Ph$ | 2 | — | \multicolumn{3}{c}{USED WITHOUT CHARACTERIZATION} |
| $C_2H_5$ | $CH_3$ | $CH_3$ | Cl | H | H | 2 | 101–120[b] | 58.66 (58.39) | 6.55 6.53 | 6.61 6.49) |
| [d]$CH_3$ | $C_2H_5$ | $C_2H_5$ | Cl | H | $CH_2Ph$ | 2 | 104–107[c] | 61.21 (61.63) | 6.06 6.11 | 4.41 4.35) |
| $CH_3$ | $C_2H_5$ | $C_2H_5$ | Cl | H | H | 2 | 185–187[a] | 55.51 (55.81) | 6.30 6.37 | 5.91 6.00) |

[a]Hydrochloride;
[b]Hemihydrate;
[c]Fumarate;
[d]starting beta-keto ester prepared by analogous method to Example 22(i).

PREPARATION 2

2-Chloro-3-fluorobenzaldehyde (i) To a stirred solution of 2-(3-fluorophenyl)-4,4-dimethyloxazoline (36.7 g) in dry tetrahydrofuran (500 ml.) at −65° C. was added dropwise n-butyl-lithium (119 ml. of 1.6M solution in hexane). The solution was stirred at the same temperature for 1 hour and then a solution of 4-toluenesulphonic chloride (36.2 g.) in dry tetrahydrofuran (250 ml.) was added over 45 minutes, maintaining the temperature below −50° C. The mixture was stirred at −50° C. for 1 hour and then allowed to warm up to room temperature and stirred for a further 2 hours. An excess of water was added and the mixture was evaporated to a low volume and extracted several times with diethyl ether. The combined extracts were washed with diluted sodium hydroxide solution, water and then dried over sodium sulphate. Evaporation of the solvent gave an oil which was distilled to give 2-(2-chloro-3-fluorophenyl)-4,4-dimethyloxazoline (29.0 g.), b.p. 138°–140° C. at 15 m.m. Found: C, 57.93; H, 4.77; N, 6.20. $C_{11}H_{11}ClFNO$ requires: C, 58.03; H, 4.87; N, 6.15%.

(ii)
2-(2-Chloro-3-fluorophenyl)-3,4,4-trimethyloxazolinium iodide

Iodomethane (9.4 g.) was added dropwise to a stirred solution of the above product (10.0 g.) in nitromethane (22 ml.). The mixture was stirred at 70° C. for 4 hours, cooled and diluted with diethylether. The solid was filtered off, washed with diethyl ether and dried to give the title product (15.5 g.), m.p. 197° C. (decomp.). Found: C, 38.83; H, 3.67; N, 3.67. $C_{12}H_{14}ClFINO$ requires: C, 38.99; H, 3.82; N, 3.79%.

(iii) 2-Chloro-3-fluorobenzaldehyde

The above product (15.5 g) was suspended in ethanol (50 ml) at 5° C. and sodium borohydride (1.6 g) was added portionwise with stirring. The mixture was stirred at 5° for 15 minutes and then at room temperature for 2 hours to give a clear solution. The solution was evaporated and the residue was dissolved in 2N hydrochloric acid (50 ml), heated to 50° C. for a few minutes and cooled. The resulting oil was extracted with diethyl ether. The ether extracts were washed with water, dried over sodium sulphate and evaporated. The residue was distilled to give 2-chloro-3-fluorobenzaldehyde (5.0 g), b.p. 86°–88° C. at 15 m.m. Found: C, 53.16; H, 2.54. $C_7H_4ClFO$ requires: C, 53.02; 2.54%.

We claim:
1. A dihydropyridine selected from those of the formulae

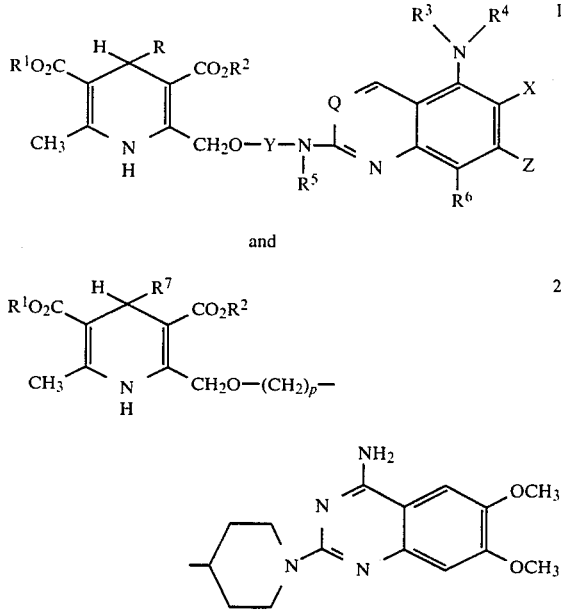

and a pharmaceutically acceptable acid addition salt thereof, wherein R is selected from the group consisting of chlorothienyl and mono- and disubstituted phenyl wherein said substituents are each selected from the group consisting of fluoro, chloro, bromo and trifluoromethyl; $R^1$ and $R^2$ are each alkyl having one to three carbon atoms; $R^3$ and $R^4$ when considered separately are each selected from the group consisting of hydrogen and alkyl having one to three carbon atoms; $R^3$ and $R^4$ when considered together with the nitrogen to which they are attached are piperidine or pyrrolidine; $R^5$ is selected from the group consisting of alkyl having one to three carbon atoms and 2-hydroxyethyl; $R^6$ is selected from the group consisting of hydrogen and methoxy; X and Z are each selected from the group consisting of hydrogen and methoxy; Y is alkylene having two to three carbon atoms; $R^7$ is selected from the group consisting of chlorophenyl and trifluoromethylchlorophenyl; p is an integer of 0 or 1; and Q is N.

2. A compound of claim 1, formula 1.

3. A compound of claim 2, wherein $R^1$ is methyl and $R^2$ is ethyl; $R^3$ and $R^4$ are each hydrogen; $R^5$ is alkyl having one to three carbon atoms; $R^6$ is hydrogen; X and Z are methoxy; and Y is ethylene.

4. The compound of claim 3, wherein $R^5$ is methyl and R is 2-chlorophenyl.

5. The compound of claim 3, wherein $R^5$ is methyl and R is 2-chloro-3-fluorophenyl.

6. The compound of claim 3, wherein $R^5$ is methyl and R is 2,3-dichlorophenyl.

7. The compound of claim 3, wherein $R^5$ is methyl and R is 2-chloro-3-trifluoromethylphenyl.

8. The compound of claim 3, wherein $R^5$ is methyl and R is 2,3-difluorophenyl.

9. The compound of claim 3, wherein $R^5$ is methyl and R is 2-fluoro-3-chlorophenyl.

10. The compound of claim 3, wherein $R^5$ is methyl and R is 2-bromophenyl.

11. The compound of claim 3, wherein $R^5$ is methyl nd R is 2-trifluoromethylphenyl.

12. A compound of claim 1, formula 2.

13. A compound of claim 12, wherein $R^1$ is methyl and $R^2$ is ethyl.

14. The compound of claim 13, wherein p is O and $R^7$ is 2-chlorophenyl.

15. A pharmaceutical composition comprising an effective antihypertensive amount of a compound according to claim 1 together with a pharmaceutically acceptable diluent or carrier.

16. A method for treating hypertension in a mammal which comprises administering to said mammal an effective antihypertensive amount of a compound according to claim 1.

* * * * *